United States Patent [19]

Nakano et al.

[11] Patent Number: 5,316,769
[45] Date of Patent: May 31, 1994

[54] DRUG FOR PREVENTING AND TREATING FISH DISEASES

[75] Inventors: Satoru Nakano, Tsuchiura; Takeo Oshima, Tokyo; Masaaki Okada; Kiyohiko Kunugita, both of Tsukuba, all of Japan

[73] Assignee: Fujisawa Pharmaceutical Co., Ltd., Osaka, Japan

[21] Appl. No.: 859,708

[22] PCT Filed: Dec. 11, 1990

[86] PCT No.: PCT/JP90/01612

§ 371 Date: Aug. 27, 1992

§ 102(e) Date: Aug. 27, 1992

[87] PCT Pub. No.: WO91/09611

PCT Pub. Date: Jul. 11, 1991

[30] Foreign Application Priority Data

Dec. 27, 1989 [JP] Japan .................. 1-342111

[51] Int. Cl.$^5$ ................................ A23K 1/17
[52] U.S. Cl. ........................... 424/442; 424/439
[58] Field of Search ........... 540/455; 424/439, 442; 514/450

[56] References Cited

U.S. PATENT DOCUMENTS 3,923,780 12/1975 Imanaka et al. .............. 540/455
4,209,518 6/1980 Mine et al. .................. 424/250

FOREIGN PATENT DOCUMENTS 48-39497 6/1973 Japan .

Primary Examiner—Thurman K. Page
Assistant Examiner—Jyothsna Venkat
Attorney, Agent, or Firm—Oblon, Spivak, McClelland, Maier & Neustadt

[57] ABSTRACT

This invention relates to a prophylactic/therapeutic composition comprising a compound of the general formula:

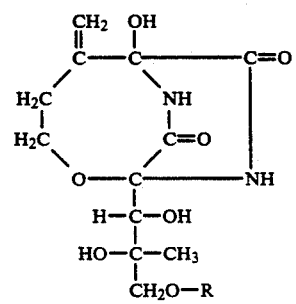

(wherein R means an alkanoyl group; a benzoyl group optionally having 1 or more substituent groups selected the group consisting of lower alkyl groups and halogen atoms; a phenylacetyl group; or a cyclohexanecarbonyl group) as an active ingredient, a method for prophylaxis and therapy of fish diseases which comprises administering a food supplemented with said compound to fish, and a fish food containing the same compound. The above composition exhibits beneficial efficacy as a prophylactic/therapeutic agent for fish diseases.

4 Claims, No Drawings

DRUG FOR PREVENTING AND TREATING FISH DISEASES

TECHNICAL FIELD

The present invention relates to a prophylactic/therapeutic agent for diseases in fish (fish diseases) and more particularly to a composition for the prevention and therapy of fish diseases which comprises a compound of the following general formula (I) as an active ingredient:

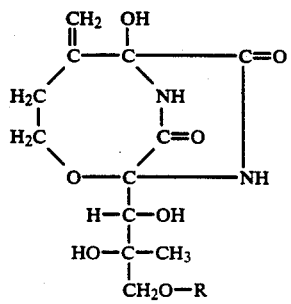

(wherein R means an alkanoyl group, a benzoyl group optionally having one or more substituent groups selected from among lower alkyl groups and halogen atoms; a phenylacetyl group; or a cyclohexanecarbonyl group).

BACKGROUND ART

Recent years have seen a great flourishing of aquiculture (culture of saltwater fish and freshwater fish) with the attendant outbreaks of various fish diseases. For the prevention and treatment of such fish diseases, taking pseudotuberculosis in yellowtail as an example, antibacterial agents such as ampicillin, oxolinic acid and the like are frequently employed. However, the common usage of these antibacterial agents is presenting the problem that pathogenic bacteria resistant to these antibacterial agents have emerged with increasing frequencies.

There exists, therefore, a true need for development of new antibacterial agents for the prevention and therapy of fish diseases, which do not have cross resistance with the conventional drugs and are active against such resistant microorganisms.

To resolve this problem, the inventors of the present invention contemplated the use of bicozamycin [the same substance as WS-4545 substance which is produced by certain microorganisms of the genus Streptomyces (Japanese Publication of Examined Patent Application No. 29158/1973)] but found that this substance was not satisfactory in the absorption from the intestinal tract.

Meanwhile, certain esters synthesized for improving the absorption of bicozamycin after oral administration [the same substances as acylated WS-4545 substance (Japanese Publication of Unexamined Patent Application No. 39497 (1973)] fulfilled the need (The Journal of Antibiotics Vol. XXV, No. 10, pp. 576–581) but application of such bicozamycin esters to fish has been refrained from for the following reason. Thus, drugs for fish are usually administered as incorporated in a raw fish mince but it was generally suspected that if an ester of bicozamycin be administered to fish, especially yellowtail, in this manner, the ester would be hydrolyzed back to bicozamycin by the esterase occurring in the fish mince so that the object of improving the oral absorption of the drug would not be accomplished. (Actually, when a known ester of ampicillin, viz. bacampicillin, is incorporated in a fish mince before administration, it is decomposed in the mince).

Under the circumstances, the inventors of the present invention dared to experimentally administer a bicozamycin ester [compound (I)] to fish in the above manner and found surprisingly that the ester was not substantially decomposed in the fish mince but was well absorbed and retained in high concentrations for long in the fish blood. The finding was followed by further research which has culminated in the present invention.

DISCLOSURE OF INVENTION

The present invention has as its object to overcome the above-mentioned problem and is directed to a prophylactic/therapeutic composition for fish diseases comprising said compound (I) as an active ingredient.

The compound (I) to be used in accordance with the present invention is, as aforesaid, a per se known compound. Moreover, bicozamycin as the starting material of this compound (1) is known as an antibiotic produced by *Streptomyces sapporonensis* ATCC 21532 as disclosed in Japanese Publication of Examined Patent Application No. 29158/1973 referred to above.

The above producer strain is available from:

Depository organ: American Type Culture Collection

Address: Parklawn Drive 12301, Rockville, Md., U.S.A.

Deposit date: April 21, 1970

Accession number: ATCC 21532

Referring, now, to compound (I), preferred examples of said alkanoyl group include acetyl, propionyl, butyryl, isobutyryl, valeryl, isovaleryl, octanoyl, palmitoyl, etc.; preferred examples of said lower alkyl group include methyl, ethyl, propyl, etc.; and preferred examples of said halogen atom include chlorine, bromine, and iodine.

The following is a partial listing of representative species of compound (I) which can be used in the present invention.

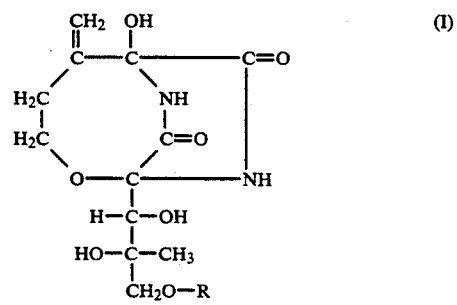

| Compound No. | R |
|---|---|
| 1 | —CO—⌬ |

-continued

| Compound No. | R |
|---|---|
| 2 | 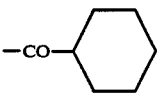 |
| 3 | 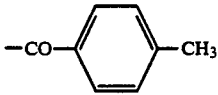 |
| 4 | 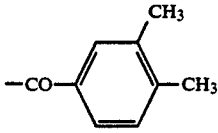 |
| 5 | 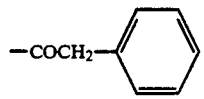 |
| 6 | 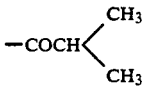 |
| 7 | 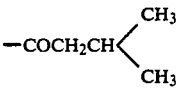 |
| 8 | 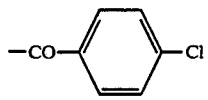 |
| 9 | —CO(CH$_2$)$_{14}$CH$_3$ |
| 10 | —COCH$_2$CH$_2$CH$_3$ |

The fishes and fish diseases for which the prophylactic/therapeutic composition of the present invention is useful include, inter alia, pseudotuberculosis (*Pasteurella piscicida*) in yellowtail and horse mackerel, vibriosis (*Vibrio anguillarum*) in yellowtail, ayu and sea bream, edwardsiellosis (*Edwardsiella tarda*) in Japanese eel, flatfish and sea bream, and furunculosis (*Aeromonas salmonicida*) in rainbow trout.

This prophylactic/therapeutic composition for fish diseases can be prepared either by processing compound (I) into a dosage form such as a powder, dust, microfine granule, granule, fine granule, tablet, liquid, pellet or syrup with or without a solid, semi-solid or liquid vehicle or by supplementing a fish food comprising formulated feed with said compound (I) or said dosage form.

The vehicle includes, among others, raw fish mince (e.g. minced mackerel, sardine, sand lance, saury, Alaska pollack, squid, etc.), formulated feed based on fishmeal, soybean cake, yeast, wheat flour, vitamins, etc., and such other conventional vehicles as lactose, sucrose, glucose, starch, talc, acid clay and so on.

In addition, emulsifiers, dispersants, gelling agents, adhesives, etc. may be added in appropriate proportions.

Such compositions containing compound (I) can be administered for the prevention or therapy of diseases in yellowtail, horse mackerel, ayu, carp, sea bream, Japanese eel, flatfish, rainbow trout and so on. For the prophylaxis or therapy of pseudoluberculosis in yellowtail, for instance, the most advantageous treatment modality will comprise, taking advantage of the stability of compound (I) in raw fish mince, adding a powdery or fine granular premix of compound (I) with said vehicle to a raw fish mince, or a mixture of such raw fish mince and formulated feed and administering the whole mixture ether as it is or as premolded into pellets or moist pellets.

The dosage and duration of administration of the present prophylactic/therapeutic composition for fish diseases are dependent on the spices and age of fish, water temperature, severity of disease, etc. For the prevention and therapy of pseudotuberculosis in yellowtail, for instance, generally 1 to 50 mg as compound (I) can be orally administered per day per kg fish body weight for 3 to 10 days.

The present prophylactic/therapeutic composition containing compound (I) shows no cross resistance with the conventional drugs, is active against resistant strains of organisms, and is stable in raw fish mince. Therefore, when it is administered to fish as mixed with a raw fish mince, the composition insures a high concentration of bicozamycin in fish blood over a protracted period of time with sufficient safety. The following test examples are intended to demonstrate the efficacy of the invention.

TEST EXAMPLE 1 the time course of blood bicozamycin concentration in yellowtail

The active compound was mixed with minced horse mackerel and administered to yellowtail in a single dose of 50 mg/kg by the free access method. At 6, 9, 12, 24, 36, 48 and 72 hours following administration, blood was taken from the heart.

The concentration of bicozamycin in the blood was then determined by the bioassay using *E. coli* BS-10 as the test organism.

The results are set forth in the following table.

| Drug | Time after administration (hrs) | | | | | | |
|---|---|---|---|---|---|---|---|
| | 6 | 9 | 12 | 24 | 36 | 48 | 72 |
| Bicozamycin | 0.29* | 0.49 | 0.59 | 1.43 | 0.54 | 0.49 | 0.27 |
| Compound 1 | 0.95 | 2.25 | 3.01 | 4.86 | 8.77 | 4.63 | 4.67 |

*μg/ml (mean of n = 5)

TEST EXAMPLE 2 stability in enzyme solutions—1

Each test drug was dissolved in water at a final concentration of 2000 μg/ml.

Then, 0.1 ml portions of each solution were added to 0.9 ml portions of various enzyme solutions.

The enzyme solutions were prepared as follows.
Deionized water: an enzyme-free control
Yellowtail plasma: The blood was taken from the heart of yellowtail into a heparinized syringe and centrifuged at 3000 rpm for 15 minutes to obtain the plasma.
Yellowtail liver homogenate: The liver was taken from live cultured yellowtail, crushed and homogenized.
Yellowtail intestine homogenate: The intestine was taken from live cultured yellowtail, crushed and homogenized.

Swine esterase: A commercial swine esterase (Sigma) was diluted 50-fold with water.

Minced mackerel: Fresh mackerel were purchased and the whole fish was crushed and minced mechanically. The minced fish was homogenized with 2 volumes of water and centrifuged at 3,000 rpm for 15 minutes and the supernatant was used as the enzyme solution.

Minced sardine: Prepared in the same manner as minced mackerel

Minced saury: Prepared in the same manner as minced mackerel

The drug solution was mixed with the enzyme solution and the reaction was carried out at 25° C. for 2 hours.

To quench the enzymatic reaction, 1.0 ml of methanol was added.

The reaction mixture was stirred gently and centrifuged at 6,400 rpm for 5 minutes. A paper disk was immersed in the supernatant and the concentration of ampicillin, cefteram (the parent compound of cefteram pivoxil), or bicozamycin, as the case may be, was determined by the bioassay using $E.\ coli$ BS-10 as the test strain.

The results are set forth in the following table. The figures shown are the rates of conversion of the compounds of the invention to bicozamycin.

umes of water and centrifuged at 3,000 rpm for 15 minutes. The supernatant was used as the enzyme solution.

Yellowtail serum: The blood was taken from the heart of yellowtail into a syringe, allowed to stand at room temperature for 1 hour and, then, centrifuged at 3000 rpm for 15 minutes to obtain the serum.

Rainbow trout plasma: The blood was taken from the heart of rainbow trout into a heparinized syringe and centrifuged at 3,000 rpm for 15 minutes to obtain the plasma.

The drug solution was mixed with the enzyme solution and the reaction was carried out at 30° C. for 3 hours.

To quench the enzymatic reaction, 0.4 ml of methanol was added.

After gentle stirring, the reaction mixture was centrifuged at 6,400 rpm for 5 minutes. A paper disk was immersed in the supernatant and the concentration of bicozamycin was determined by the bioassay using $E.\ coli$ BS-10 as the test strain.

The results are set forth in the following table. The figures shown are the rates of conversion of the compounds of the invention to bicozamycin.

| Enzyme solution | Compound 1 | Compound 3 | Compound 4 | Compound 5 | Compound 6 | Compound 7 | Compound 2 | Compound 8 |
|---|---|---|---|---|---|---|---|---|
| Deionized water | <0.2 | <0.2 | <0.2 | 1 | <0.2 | <0.2 | <0.2 | <0.2 |
| Swine esterase | 100 | 100 | 50 | 100 | 100 | 50 | 100 | 100 |
| Raw fish mince (mackerel + sardine) | <0.2 | <0.2 | 2 | 3 | <0.2 | <0.2 | 6 | 2 |
| Yellow serum | 13 | 13 | 13 | 25 | 50 | 13 | 100 | 1 |
| Rainbow trout plasma | 100 | 100 | 50 | 50 | 100 | 100 | 100 | 100 | figures shown are the rates of conversion of bacampicillin to ampicillin, of cefteram pivoxil to its parent compound (Journal of Japan Society of Chemotherapy Vol. 34, S-2, pp. 44–60, 1986) and of the compound of the invention to bicozamycin.

| Enzyme solution | Bacampicillin | Cefteram pivoxil | Compound 1 | Compound 10 | Compound 9 |
|---|---|---|---|---|---|
| Deionized water | 50 | 89 | <3 | <3 | <3 |
| Yellowtail plasma | 100 | | <3 | 13 | <3 |
| Yellowtail liver homogenate | 100 | | <3 | <3 | <3 |
| Yellowtail intestine homogenate | 100 | | <3 | <3 | <3 |
| Swine esterase | 100 | 100 | 100 | 100 | 6 |
| Minced mackerel | 100 | | <3 | <3 | <3 |
| Minced sardine | 100 | 84 | <3 | <3 | <3 |
| Minced saury | | 76 | <1 | | |

TEST EXAMPLE 3 stability in enzyme solutions—2

Each test drug was dissolved in water at a final concentration of 1000 µg/ml.

Then, 0.04 ml portions of each solution were added to 0.36 ml portions of various enzyme solutions.

The enzyme solutions were prepared as follows

Deionized water: An enzyme-free control

Swine esterase: A commercial swine esterase (Sigma) was diluted 50-fold with water.

Raw fish mince: Fresh mackerel and sardine were purchased and equal parts of the respective whole fishes were crushed and mixed. The mixture was minced mechanically, homogenized with two vol-

TEST EXAMPLE 4

Comparison with conventional drugs

Yellowtail weighing about 200 g, which had developed pseudotuberculosis in the field, were divided into 7 groups of 200 fish and treated according to the following dosage schedule. Group I: drug-free control, Group II: ampicillin 20 mg/kg, Group III oxolinic acid 30 mg/kg, Group IV: Compound 1 20 mg/kg; Group V: Compound 1 40 mg/kg; Group VI: Compound 2 20 mg/kg; and Group VII: Compound 2 40 mg/kg. The total weight of fish in each group was determined. The fish in each group were fasted for one day and, then, given a mixture of a formulated feed for yellowtail and the corresponding drug (10% in lactose), as further admixed with minced sand lance, once a day for 5 consecutive days. Dead fish were landed every day during morning hours and the number of deaths was recorded.

Furthermore, all the dead fish were autopsied to confirm that death was due to pseudotuberculosis.

The water temperature was measured daily during morning hours and recorded.

The results are set forth in the following table.

| | Group | Number of fish | Daily count of dead fish |||||||
|---|---|---|---|---|---|---|---|---|---|
| | | | Sep. 1 | 2 | 3 | 4 | 5 | 6 | 7 | 8 |
| Drug-free control | | 200 | 1 | 2 | 2 | 0 | 1 | 2 | 2 | 5 |
| Ampicillin | 20 mg/kg | 200 | 2 | 0 | 0 | 2 | 2 | 0 | 2 | 3 |
| Oxolinic acid | 30 mg/kg | 200 | 2 | 1 | 1 | 0 | 0 | 0 | 0 | 4 |
| Compound 1 | 20 mg/kg | 200 | 1 | 1 | 0 | 0 | 0 | 0 | 0 | 0 |
| | 40 mg/kg | 200 | 2 | 1 | 0 | 0 | 0 | 0 | 0 | 0 |
| Compound 2 | 20 mg/kg | 200 | 1 | 0 | 0 | 0 | 1 | 0 | 0 | 0 |
| | 40 mg/kg | 200 | 3 | 3 | 0 | 0 | 0 | 0 | 0 | 0 |
| Remarks | | | | | | | | | | |
| Dosing | | | ↑ | ↑ | ↑ | ↑ | ↑ | | | |
| Water temperature (°C.) | | | 23.0 | 23.0 | 22.9 | 22.8 | 22.2 | 23.5 | 24.0 | 24.0 |

TEST EXAMPLE 5

Comparison with bicozamycin

Yellowtail weighing about 200 g, which had developed pseudotuberculosis in the field, were divided into 4 groups of 300~320 fish and treated according to the following dosage schedule. Group I: drug-free control, Group II: bicozamycin 20 mg/kg, Group III compound 1 20 mg/kg, Group IV: Compound 2 20 mg/kg. The total weight of fish in each group was determined. The fish in each group were starved for one day and, then, given a mixture of a formulated feed for yellowtail and the corresponding drug (10% in lactose), as further admixed with minced sand lance, once a day for 5 consecutive days. Dead fish were landed every day during morning hours and the number of deaths was recorded. Furthermore, all the dead fish were autopsied to confirm that death was due to pseudotuberculosis.

The water temperature was measured daily during morning hours and recorded.

The results are set forth in the following table.

unit and 200 kg of minced sand lance for 5 consecutive days. The above regimen accomplishes the object of preventing and curing pseudotuberculosis in yellowtail.

EXAMPLE 2

A powder is prepared by mixing 6.7 parts by weight of Compound 1 [5 parts by weight of bicozamycin(potency)] with 93.3 parts by weight of lactose.

About 15,000 yellowtail weighing 200 g on the average or a total of 3 tons are given moist pellets (columnar pellets prepared by mixing minced sardine with a formulated feed power based on fish meal in a ratio of 6:4 and pelletizing the mixture mechanically) supplemented with 300 g of the above powder for 5 consecutive days. This regimen accomplishes the object of preventing and curing pseudotuberculosis in yellowtail.

INDUSTRIAL APPLICABILITY

Constituted as above, the present invention can be used as a prophylactic/therapeutic agent, particularly a therapeutic agent, for fish diseases to thereby increase the crop of fish.

What is claimed is:

1. A fish food which is a moist pellet prepared from a mixture of fish mince and formulated feed, containing a compound of the formula:

| | Group | Number of fish | Daily count of dead fish ||||||
|---|---|---|---|---|---|---|---|---|---|
| | | | Sep. 15 | 16 | 17 | 18 | 19 | 20 | 21 |
| Drug-free control | | 320 | — | 49 | 43 | 23 | 21 | 6 | 4 |
| Bicozamycin | 20 mg/kg | 300 | — | 57 | 32 | 32 | 12 | 4 | 1 |
| Compound 1 | 20 mg/kg | 300 | — | 41 | 17 | 14 | 5 | 1 | 1 |
| Compound 2 | 20 mg/kg | 300 | — | 41 | 11 | 8 | 1 | 3 | 0 |
| Remarks | | | | | | | | | |
| Dosing | | | ↑ | ↑ | ↑ | ↑ | ↑ | | |
| Water temperature (°C.) | | | 26.0 | 27.0 | 27.5 | 27.5 | 28.0 | 27.5 | 28.5 |

EXAMPLE 1

A powder is prepared by mixing 6.7 parts by weight of Compound 1 [5 parts by weight of bicozamycin(potency)] with 93.3 parts by weight of lactose.

Using 100 g of the powder as a daily dose unit, about 20,000 yellowtail weighing 50 g on the average or a total of 1 ton are fed with a mixture of the above dose

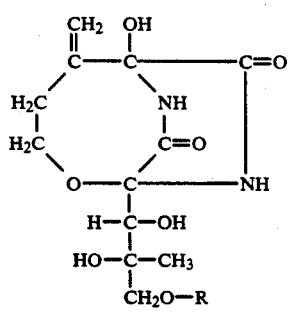

where R is an alkanoyl group; a benzoyl group optionally having one or more substituent groups selected from the group consisting of lower alkyl groups, halogen atoms, penylacetyl group and cyclohexanecarbonyl group.

2. A fish food as claimed in claim 1 wherein R is benzoyl or cyclohexanecarbonyl.

3. A fish food which is a mixture of fish mince and formulated feed, containing a compound of the formula:

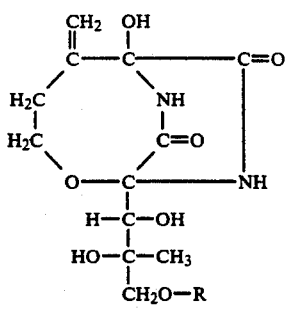

where R is an alkanoyl group; a benzoyl group optionally having one or more substituent groups selected from the group consisting of lower alkyl group, halogen atoms phenylacetyl group and cyclohexanecarbonyl group.

4. A fish food as claimed in claim 3, wherein R is benzoyl or cyclohexanecarbonyl.

* * * * *

UNITED STATES PATENT AND TRADEMARK OFFICE
CERTIFICATE OF CORRECTION

PATENT NO. : 5,316,769

DATED : May 31, 1994

INVENTOR(S) : Nakano et al

It is certified that error appears in the above-identified patent and that said Letters Patent is hereby corrected as shown below:

Claim 1, column 9, lines 16-21: "where R is an alkanoyl group; a benzoyl group optionally having one or more substituent groups selected from the group consisting of lower alkyl groups, halogen atoms, penylacetyl group and cyclohexane-carbonyl group." should read --where R is an alkanoyl group; a benzoyl group optionally having one or more substituent groups selected from the group consisting of lower alkyl groups and halogen atoms; a phenylacetyl group; or a cyclo-hexanecarbonyl group.--.

Claim 3, column 10, lines 17-21: "where R is an alkanoyl group; a benzoyl group optionally having one or more substituent groups selected from the group consisting of lower alkyl group, halogen atoms phenylacetyl group and cyclohexanecarbonyl group." should read --where R is an alkanoyl group; a benzoyl group optionally having one or more substituent groups selected from the group consisting of lower alkyl groups and halogen atoms; a phenylacetyl group; or a cyclohexanecarbonyl group.--.

Signed and Sealed this

First Day of November, 1994

*Attest:*

BRUCE LEHMAN

*Attesting Officer*  *Commissioner of Patents and Trademarks*